(12) United States Patent
Temmerman et al.

(10) Patent No.: US 11,058,439 B2
(45) Date of Patent: Jul. 13, 2021

(54) SURGICAL INSTRUMENT

(71) Applicant: Olivier Paul Pieter Temmerman, Bloemendaal (NL)

(72) Inventors: Olivier Paul Pieter Temmerman, Bloemendaal (NL); Micha Ilan Paalman, Amsterdam (NL)

(73) Assignee: Olivier Paul Pieter Temmerman, Bloemendaal (NL)

( * ) Notice: Subject to any disclaimer, the term of this patent is extended or adjusted under 35 U.S.C. 154(b) by 292 days.

(21) Appl. No.: 16/253,101

(22) Filed: Jan. 21, 2019

(65) Prior Publication Data
US 2019/0150956 A1 May 23, 2019

Related U.S. Application Data

(63) Continuation of application No. PCT/NL2017/050446, filed on Jul. 4, 2017.

(30) Foreign Application Priority Data

Jul. 21, 2016 (NL) ..................................... 2017203

(51) Int. Cl.
*A61B 17/16* (2006.01)
*A61B 17/88* (2006.01)
*A61B 17/00* (2006.01)

(52) U.S. Cl.
CPC ...... *A61B 17/1657* (2013.01); *A61B 17/1604* (2013.01); *A61B 17/1664* (2013.01); *A61B 17/8866* (2013.01); *A61B 2017/0046* (2013.01)

(58) Field of Classification Search
CPC .......................... A61B 17/1604; A61B 17/1657
See application file for complete search history.

(56) References Cited

U.S. PATENT DOCUMENTS

| | | | |
|---|---|---|---|
| 4,873,969 A | 10/1989 | Huebsch | |
| 5,720,750 A * | 2/1998 | Koller | A61F 2/4684 606/85 |
| 6,126,664 A | 10/2000 | Troxell et al. | |
| 6,264,660 B1 | 7/2001 | Schmidt et al. | |
| 6,478,805 B1 | 11/2002 | Marino et al. | |
| 2005/0090829 A1 | 4/2005 | Martz et al. | |
| 2005/0192582 A1 | 9/2005 | Reay-Young | |
| 2006/0074426 A1 * | 4/2006 | Lieberman | A61B 17/1671 606/79 |
| 2007/0073301 A1 | 3/2007 | Lieberman | |

FOREIGN PATENT DOCUMENTS

| | | |
|---|---|---|
| WO | 94/22380 | 10/1994 |
| WO | 2018/016943 | 1/2018 |

* cited by examiner

*Primary Examiner* — Samuel S Hanna
(74) *Attorney, Agent, or Firm* — Peacock Law P.C.; Justin Muehlmeyer

(57) ABSTRACT

A surgical instrument for use on a patient's bone is provided and according to one embodiment the surgical instrument comprises a support rod or bar, and a breaking tool that is provided at an extremity of the support rod or bar, which breaking tool comprises a nose and a knife or chisel, wherein between the nose and the knife or chisel a room is provided which is arranged to receive material that is to be removed from the bone, wherein the knife or chisel has at least two surfaces facing the nose, which surfaces merge into a joint crossing line substantially dividing the knife or chisel into two parts on opposite sides of the crossing line, so as to provide a splitting operability to the knife or chisel.

11 Claims, 2 Drawing Sheets

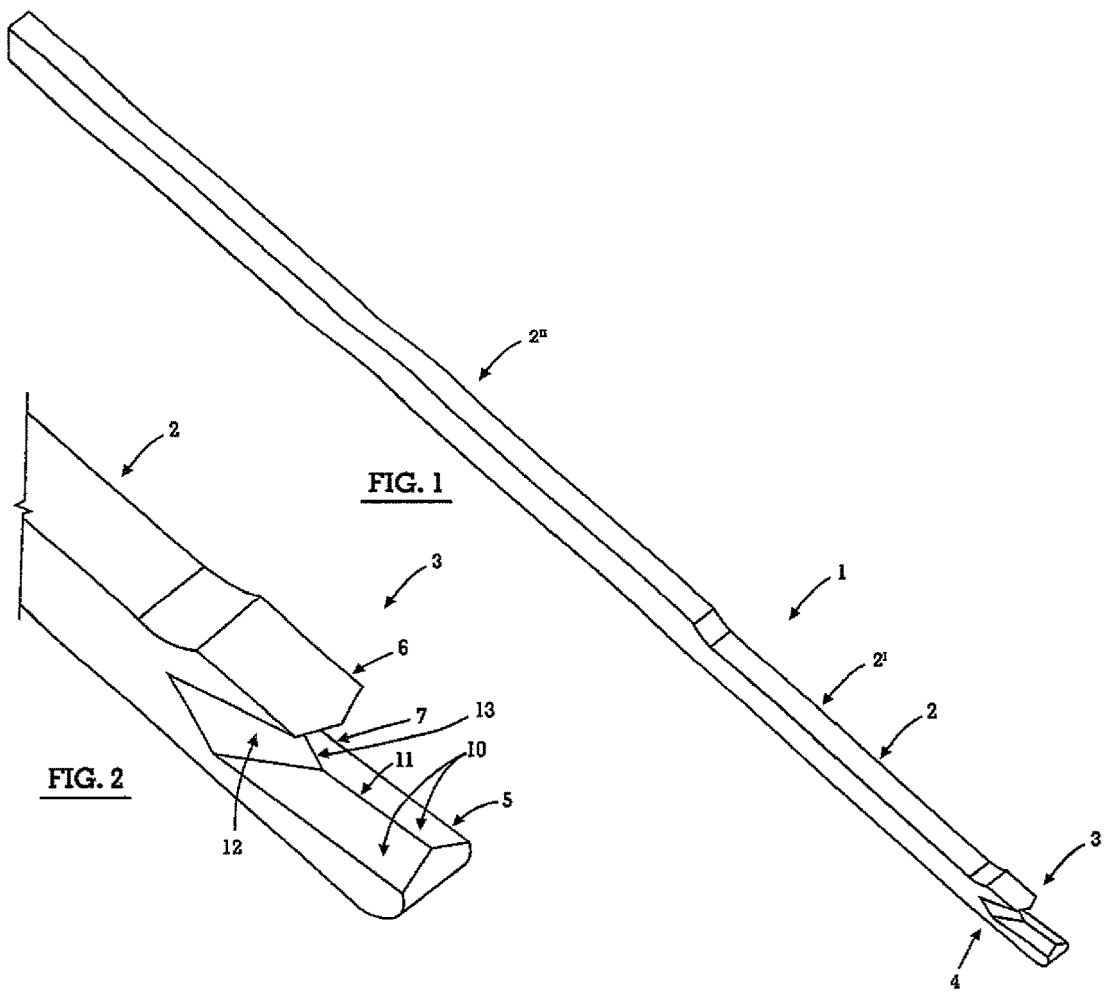
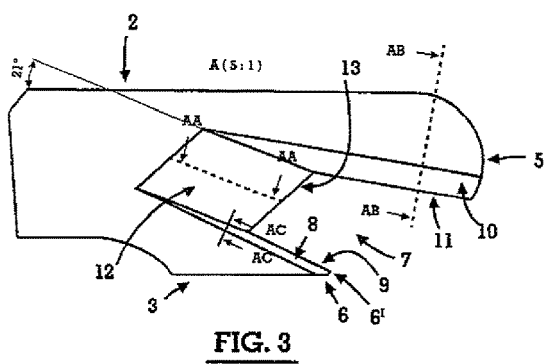
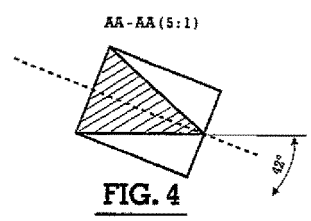
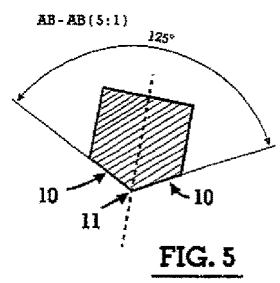
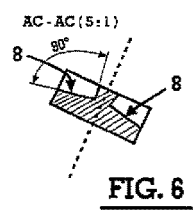

SURGICAL INSTRUMENT

CROSS-REFERENCE TO RELATED APPLICATIONS

This application is a continuation application of International Application No. PCT/NL2017/050446, entitled "SURGICAL INSTRUMENT COMPRISING A BREAKING TOOL", filed on Jul. 4, 2017, which claims priority to and the benefit of Netherlands Application No. 2017203, entitled "SURGICAL INSTRUMENT" filed on Jul. 21, 2016, and the specification and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Field of the Invention (Technical Field)

The invention relates to a surgical instrument for use on a patient's bone, comprising a support rod or bar, and a breaking tool provided at an extremity of the support rod or bar.

BRIEF SUMMARY OF THE INVENTION

There are numerous applications for such a surgical instrument, for instance for removal of bone that has to be removed from other bone, or for removal of cured bone cement, such as used in orthopedic surgery. The surgical instrument of the invention will hereinafter be discussed with reference to the removal of cured bone cement, albeit understood that the use of the surgical instrument of the invention is not restricted thereto.

WO94/22380 discloses a disposable surgical instrument for use in removing uncured bone cement. The instrument known from WO94/22380 is used immediately after cementing a bone in which an implant is to be inserted, such as when placing a new hip joint. By using the cement, part of the implant will be tightly fixed to the thighbone. This known instrument is used to remove excess cement before it has cured. The instrument has a handle in the middle with sculpting tools at opposing ends of the handle.

US2005/0090829 discloses a chisel for preparing adjacent vertebrae for insertion of a spinal implant into a disc space defined by the vertebrae, comprising a shank, a cutting head coupled to the distal end of the shank and provided with a cutting edge, and a guide member extending from the head distal to the cutting edge for insertion into the disc space.

U.S. Pat. No. 6,126,664 discloses a device for removing a section of bone comprising an osteotome with a distal end and provided with the cutting element for removal of a section of bone, and a pedicle finder with an osteotome guide configured and dimensioned to sliding the engage a portion of the osteotome.

U.S. Pat. No. 6,478,805 discloses a system for removing cutting tissue from the inner bore of a surgical rongeur or suction punch, comprising an elongated tubular member, a tubular cutting element, and a hollow tube extending inwardly from a distal end of the elongated tubular member, wherein a suctioning source is applied to suck tissue from the inner bore of the elongated tubular member.

The invention relates to a different type of tool which in one of its applications can be used for removing cured bone cement. The instrument is then used when the implant has worn out and has to be replaced. When that happens also the previously applied bone cement needs to be removed, and it is an object of the invention to provide a suitable tool therefore.

From the prior art different ways of removing cured bone cement are known.

US2005/0192582 discloses a bone block harvester comprising a body having a proximal end and a distal end, a cutter disposed at the distal end of the harvester, and a cutting guide coupled to the cutter and having a tissue contact surface spaced from the cutter.

U.S. Pat. No. 4,873,969 teaches the removal of bone cement from a bone cavity during a prosthetic revision, using a surgical instrument having a heated tip at its working end which is inserted into the bone cement, wherein an element for heating the tip is carried by the instrument to heat the tip to a temperature sufficient to mold one or more grooves into the bone cement upon direct contact by the heated tip of the surgical instrument; and wherein after removal of the heated tip the bone cement is allowed to reharden so as to produce weakened areas in the bone cement in the vicinity of the molded grooves. Thereafter a surgical impact type chisel is placed against the sections of the bone cement between said weakened areas, and removal of the sections of bone cement is then performed by direct impacting of the chisel.

U.S. Pat. No. 6,264,660 teaches a surgical instrument for the mechanical removal of bone cement comprising a longitudinal housing comprising a tubular cylinder in which a piston projectile can be reciprocated, wherein driving means are provided for driving the piston projectile from a proximal end of the cylinder toward a distal end of the cylinder and wherein a shock wave transmission probe is applied having a chisel tip at its distal end and a proximal end adapted to receive impact forces generated by said piston projectile, said driving means being constructed and arranged for accelerating said piston projection to induce a shock wave in the chisel tip which is transmitted to the bone cement.

A disadvantage of the known methods and apparatuses is that measures or features are required that complicate the devices that are used and make them more expensive. A further disadvantage is that these known devices also require very accurate positioning relative to the bone cement to be removed to avoid undesirable damage to the bone itself.

It is therefore an object of the invention to provide a relatively simple and cost-effective tool which can be used for efficient and complete removal of cured bone cement, and which can be applied by using human power only with less risk for the bone of the patient.

Another object of the invention is to gain advantages in terms of shortening the time needed for surgery that is attributable to the use of the surgical instrument, and to reduce the risk of complications that relate to unpredictable behaviour of the used surgical instrument, such as damage inflicted on the bone of the patient or to surrounding tissue. Correspondingly and in general an object of the invention is to reduce risks for the patient in connection with the surgery in which the surgical instrument is used.

Accordingly, the invention proposes a surgical instrument having the features of one or more of the appended claims.

In a first aspect of the invention wherein the breaking tool of the surgical instrument comprises a preferably elongated nose and a knife or chisel, and wherein between the nose and the knife or chisel a room is provided which is arranged to receive part of the material that is to be removed from the bone, the surgical instrument is provided with the feature that the knife or chisel has at least two surfaces facing the nose, which surfaces merge into a joint crossing line substantially dividing the knife or chisel into two, preferably equal, parts on opposite sides of the crossing line, so as to provide a splitting operability to the knife or chisel. The knife or chisel than operates as a plough on the material to be removed from the bone. The removed material can in certain applications be bone but usually it is cured bone cement which has to be removed before placing of a new implant can be executed. After appropriate placement of the instrument of the invention with the knife or chisel at the separation between the bone that has to remain and the material that has to be removed, the surgical instrument then only needs to be advanced to arrange that the material which is to be removed is received in said room between the nose and the knife or chisel, and is broken loose. The nose then secures that no adversery forces that are caused by advancing the surgical instrument will come to act on the bone that has to remain intact. The construction of the surgical instrument of the invention also arranges that advancing the surgical instrument will occur in a defined straight line.

Preferably the knife or chisel is shorter than the nose. This promotes the avoidance of said adversely forces on the bone as well as the instrument's advancing in a straight line.

It is preferred that the knife or chisel is wedge shaped, wherein in a direction pointing away from the support rod or bar, a surface or surfaces of the knife or chisel facing the nose taper away from said nose to provide the room with an increasing width dimension in said direction pointing away from the support rod or bar. The wedge-shaped knife or chisel is very handy to support its placement between the bone and the material, particularly the bone cement, which is meant to be removed, whereas the increasing width dimension of the room at the frontal portion of the instrument makes receiving the material to be removed therein easy.

Desirably a frontal end of the wedge-shaped knife or chisel is embodied as a flat non-sharp frontal surface. This arranges that the knife or chisel is less susceptible to becoming too blunt to continue its effective use. The strength of the frontal end of the knife or chisel is then sufficient to withstand it bending over when operating on the material that is to be removed from the bone, which would otherwise occur with a perfectly sharp frontal end of the knife or chisel.

It is further preferable that the nose has at least two surfaces facing the knife or chisel, which surfaces merge into a joint crossing line substantially dividing the nose into two, preferably equal, parts on opposite sides of the crossing line. This promotes the operability of the surgical instrument acting as a plough on the material to be removed from the bone.

Further preferably the elongated nose and the knife or chisel share a common base which has a frontal portion facing the room that is wedge shaped so as to support and enhance a splitting operability of the knife or chisel acting as a plough in the material to be removed.

It can be advantageous that the support rod or bar has a decreased width dimension in a first region adjacent to the breaking tool in comparison with a second region distant from the breaking tool in order to provide room for movement of the surgical instrument in particular surgical situations. For instance when performing an operation to replace a hip joint, the room to move the surgical instrument in the process of removing bone cement can be rather limited.

In another aspect of the invention which can be applied in combination with but also separate from the features of the surgical instrument of the invention as discussed hereinabove and specified in the appended claims 1-8, the support rod or bar is designed for mounting in a handle that is equipped to be removably placed on an extremity of said rod or bar distant from the breaking tool. The instrument of the invention can thus easily be replaced, but also its handling can be optimized by a proper design of the handle without restrictions imposed by an otherwise required integral design of the handle and breaking tool.

Replacement of the breaking tool can then easily be carried out by arranging that the handle comprises two pivotably connected handle parts defining an open position and a closed position, wherein in the open position the rod or bar is removable from the handle, and in the closed position the rod or bar is locked in the handle.

By arranging that the handle is provided with an aperture which is designed to snugly receive a part of the rod or bar, a reliable and immovable rotationally fixed placement of the support rod or bar in the handle can be secured.

Preferably at least one of the handle parts is provided with an extension designed to mate with a recess in the rod or bar when the handle parts are moved into their closed position. This effectively fixes the rod or bar in position avoiding the possibility of any longitudinal movement of the rod or bar in the handle.

Further it is preferred that the extension is eccentric so as to exert a bending force to the recess in the rod or bar when the handle parts are in the closed position. By this measure play between the rod or bar and the handle parts is effectively avoided.

BRIEF DESCRIPTION OF THE SEVERAL VIEWS OF THE DRAWINGS

The invention will hereinafter be further elucidated with reference to the drawing of an exemplary embodiment of a surgical instrument according to the invention that is not limiting as to the appended claims.

FIG. 1 shows a surgical instrument according to one embodiment of the present invention without handle;

FIG. 2 shows a detail of the instrument of FIG. 1;

FIG. 3 shows a side view of the instrument as shown in FIG. 2;

FIG. 4 shows a cross-sectional view according to the line AA-AA in FIG. 3;

FIG. 5 shows a cross-sectional view according to the line AB-AB in FIG. 3;

FIG. 6 shows a cross-sectional view according to the line AC-AC in FIG. 3; and

Whenever in the figures the same reference numerals are applied, these numerals refer to the same parts.

DETAILED DESCRIPTION OF THE INVENTION

Figure 7:
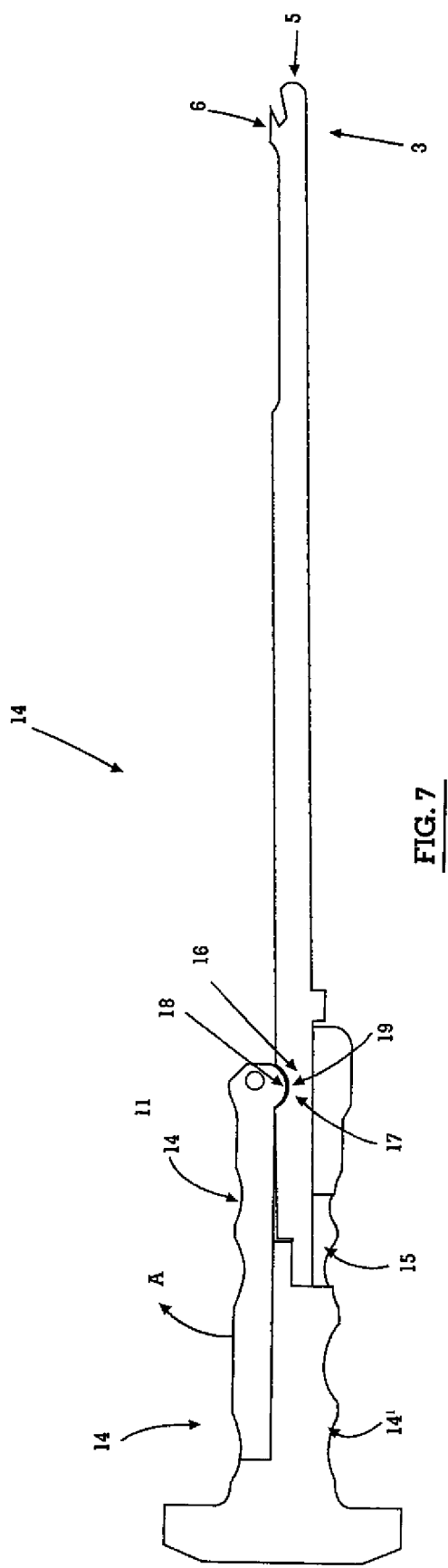
FIG. 7 shows the surgical instrument of one embodiment of the present invention with a handle.

In the following elucidation of the invention the use of the instrument will be discussed with reference to the removal of bone cement from a bone. The inventors however explicitly point out that the use of the instrument of the invention is not restricted to this application.

With reference first to FIG. 1 a surgical instrument 1 for removal of cured bone cement according to one embodiment of the present invention is shown without its handle. The handle can be fixedly attached to the instrument 1 or be removable which latter option is the preferred situation. The instrument 1 can for instance be used in orthopedic hip surgery, and comprises a support rod or bar 2, and a breaking tool 3 for the bone cement to be removed, which breaking tool 3 is provided at an extremity 4 of the support rod or bar 2. For the purpose to provide the instrument with sufficient manipulating room, the support rod or bar 2 preferably has a decreased width dimension in a first region 2' adjacent to the breaking tool 3 in comparison with a second region 2" distant from the breaking tool 3.

A detailed view of the breaking tool 3 provides FIG. 2, which shows that the breaking tool 3 comprises a nose 5 and preferably a relative to the nose 5 shorter knife or chisel 6, wherein between the nose 5 and the knife or chisel 6, a room 7 is provided which is arranged to receive part of the cured bone cement that is to be removed. FIG. 3 shows the same from a side view. FIG. 2 and in particular FIG. 3 clearly show that the knife or chisel 6 is wedge shaped. In a direction pointing away from the support rod or bar 2, a surface or surfaces 8 of the knife or chisel 6 facing the nose 5 taper away from said nose 5 to provide the room 7 with an increasing width dimension in said direction pointing away from the support rod or bar 2. This is clearly shown in FIG. 3. FIG. 3 also shows that a frontal end of the wedge-shaped knife or chisel 6 is embodied as a flat non-sharp frontal surface 6'.

It will be clear from the combination of FIG. 3 and FIG. 6 that the knife or chisel 6 has at least two surfaces 8 facing the elongated nose 5. These surfaces 8 merge into a joint crossing line 9 substantially dividing the knife or chisel 6 into two preferably equal parts on opposite sides of the crossing line 9, so as to provide a splitting operability of a plough to the knife or chisel 6 when used for instance to remove bone cement.

Also, the nose 5 has at least two surfaces 10 facing the knife or chisel 6, which surfaces 10 merge into a joint crossing line 11 substantially dividing the nose 5 into two equal parts on opposite sides of the crossing line 11, so as to further the functionality of the instrument acting as a plough when in use to remove material such as bone cement. This is clearly shown in FIGS. 2, 3 and 5.

FIGS. 2, 3 and 4 further show that the preferably elongated nose 5 and the knife or chisel 6 share a common base 12 which has a frontal portion 13 facing the room 7 that is wedge shaped so as to support and enhance the said functionality of the knife or chisel 6 acting as a plough on the material to be removed.

FIG. 7 shows that the support rod or bar 2 is designed for mounting in a handle 14 that is equipped to be removably placed on an extremity 15 of said rod or bar 2 distant from the breaking tool 3. The handle 14 comprises two pivotably connected handle parts 14', 14" defining an (not shown) open position and a closed position, wherein in the open position the rod or bar 2 is removable from the handle 14, and in the shown closed position the rod or bar 2 is locked in the handle 14. The handle 14 can be opened to enable removing of the rod or bar 2 by pivoting the handle part 14" in the direction of the arrow A away from the handle part 14'.

To secure the position of the rod or bar 2 in the handle 14, said handle is provided with an aperture 16 which is designed to snugly receive a part 17 of the rod or bar 2. In connection with this secure positioning of the rod or bar 2 in the handle 14, at least one of the handle parts, notably handle part 14" is provided with an extension 18 designed to mate with a recess 19 in the rod or bar 2 when the handle parts 14', 14" are in their closed position as shown in FIG. 7. This effectively secures against longitudinal movement of the rod or bar 2 in the handle 14. It is further preferable that the extension 18 is eccentric so as to exert a bending force to the recess 19 when the rod or bar 2 is in the closed position of the handle parts 14', 14". The back portion of the rod or bar 2 acts as a leaf spring. This removes any play of the rod or bar 2 when it is positioned in the handle 14.

Although the invention has been discussed in the foregoing with reference to an exemplary embodiment of the apparatus of the invention, the invention is not restricted to this particular embodiment which can be varied in many ways without departing from the invention. The discussed exemplary embodiment shall therefore not be used to construe the appended claims strictly in accordance therewith. On the contrary the embodiment is merely intended to explain the wording of the appended claims without intent to limit the claims to this exemplary embodiment. The scope of protection of the invention shall therefore be construed in accordance with the appended claims only, wherein a possible ambiguity in the wording of the claims shall be resolved using this exemplary embodiment.

The invention claimed is:

1. A surgical instrument for use on a patient's bone, comprising:
    a support rod or bar; and
    a breaking tool provided at an extremity of the support rod or bar, which breaking tool comprises:
    a nose and a knife or chisel, wherein between the nose and the knife or chisel a room is provided which is arranged to receive material that is to be removed from the bone, and wherein the knife or chisel has at least two surfaces facing the nose, which surfaces merge into a straight joint crossing line substantially dividing the knife or chisel into two parts on opposite sides of the crossing line, so as to provide a splitting operability to the knife or chisel;
    wherein the nose has at least two surfaces facing the knife or chisel, which surfaces merge into a straight joint crossing line substantially dividing the nose into two parts on opposite sides of the crossing line;

wherein the nose and the knife or chisel share a common base which has a frontal portion facing the room that is wedge shaped; and wherein the frontal portion of the common base comprises a straight edge that traverse both the joint crossing line of the knife or chisel and the joint crossing line of the nose.

2. The surgical instrument of claim 1, wherein the knife or chisel is wedge shaped, wherein in a direction pointing away from the support rod or bar, a surface or surfaces of the knife or chisel facing the nose taper away from said nose to provide the room with an increasing width dimension in said direction pointing away from the support rod or bar.

3. The surgical instrument of claim 1, wherein the knife or chisel is wedge-shaped and wherein a frontal end of the knife or chisel is comprises a flat non-sharp frontal surface.

4. The surgical instrument of claim 1, wherein the knife or chisel is shorter than the nose.

5. The surgical instrument of claim 1, wherein the support rod or bar has a decreased width dimension in a first region adjacent to the breaking tool in comparison with a second region distant from the breaking tool.

6. The surgical instrument of claim 5, wherein the support rod or bar is designed for mounting in a handle that is equipped to be removably placed on an extremity of said rod or bar distant from the breaking tool.

7. The surgical instrument of claim 6, wherein the handle comprises two pivotably connected handle parts defining an open position and a closed position, wherein in the open position the rod or bar is removable from the handle, and in the closed position the rod or bar is locked in the handle.

8. The surgical instrument of claim 6, wherein the handle is provided with an aperture which is designed to snugly receive a part of the rod or bar.

9. The surgical instrument of claim 7, wherein at least one of the handle parts is provided with an extension designed to mate with a recess in the rod or bar when the handle parts are moved into their closed position.

10. The surgical instrument of claim 9, wherein the extension is eccentric so as to exert a bending force to the recess in the rod or bar when the handle parts are in the closed position.

11. The surgical instrument of claim 5, wherein the room separates the nose from the knife or chisel entirely.

* * * * *